United States Patent
Xia et al.

(10) Patent No.: US 9,708,443 B2
(45) Date of Patent: Jul. 18, 2017

(54) EFFICIENT SYNTHESIS OF RIGID LADDER POLYMERS

(71) Applicant: Board of Trustees of the Leland Stanford Junior University, Palo Alto, CA (US)

(72) Inventors: Yan Xia, Stanford, CA (US); Sheng Liu, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/871,691

(22) Filed: Sep. 30, 2015

(65) Prior Publication Data

US 2016/0108169 A1   Apr. 21, 2016

Related U.S. Application Data

(60) Provisional application No. 62/057,953, filed on Sep. 30, 2014.

(51) Int. Cl.
*C08G 61/00* (2006.01)
*C08G 61/02* (2006.01)
(Continued)

(52) U.S. Cl.
CPC .......... *C08G 61/02* (2013.01); *C07D 493/22* (2013.01); *C08G 61/126* (2013.01);
(Continued)

(58) Field of Classification Search
CPC .......... C08F 32/08; C08F 32/00; C08G 61/02; C08G 61/125; C08G 2261/31; C08G 2261/1336
See application file for complete search history.

(56) References Cited

U.S. PATENT DOCUMENTS

| | | | | |
|---|---|---|---|---|
| 3,658,669 A | * | 4/1972 | Colomb, Jr. | C08J 3/246 522/117 |
| 3,817,883 A | * | 6/1974 | Campbell | C08L 21/00 524/526 |
| 6,350,832 B1 | * | 2/2002 | Bell | C08F 32/00 526/134 |

OTHER PUBLICATIONS

Kintzel, O.; Munch, W.; Schluter, A.-D. J. Org. Chem. 1996, 61, 7304-7308.*

(Continued)

*Primary Examiner* — Rip A. Lee
(74) *Attorney, Agent, or Firm* — Foley & Lardner LLP; Cliff Z. Liu

(57) ABSTRACT

A molecule includes at least one moiety represented by:

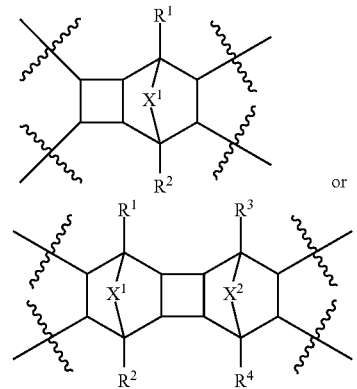

where $R^1$, $R^2$, $R^3$, and $R^4$ are independently selected from hydride group and groups different from hydride group, and $X^1$ and $X^2$ are bridging moieties including a carbon atom or a heteroatom.

19 Claims, 8 Drawing Sheets

(51) Int. Cl.
*C07D 493/22* (2006.01)
*C08G 61/12* (2006.01)

(52) U.S. Cl.
CPC . *C08G 2261/1336* (2013.01); *C08G 2261/31* (2013.01); *C08G 2261/3325* (2013.01); *C08G 2261/3342* (2013.01); *C08G 2261/41* (2013.01); *C08G 2261/62* (2013.01)

(56) References Cited

OTHER PUBLICATIONS

Chen et al. (Macromolecules 2006, 39, 3202-3209.*
Keck, C.G.; Kendall, J.L.; Caster, K.C. Adsv. Synth. Catal. 2007, 349, 165-174.*
Saunders, R.S. Macromolecules 1995, 28, 4347-4349.*
Bezzu, C.G. et al. (2012) "A Spirobifluorene-Based Polymer of Intrinsic Microporosity with Improved Performance for Gas Separation," Adv. Mater. 24:5930-5933.
Bocelli, G. et al. (1984) "Palladium-Catalyzed C-C Bond Formation Involving Aromatic C-H Activation," Journal of Organometallic Chemistry 279:225-232.
Brown, J.F., Jr. et al. (1960) "Double Chain Polymers of Phenylsilsesquioxane," J. Am. Chem. Soc. 82(23):6194-6195.
Carta, M. et al. (2013) "An Efficient Polymer Molecular Sieve for Membrane Gas Separations," Science 339(6117):303-307.
Catellani, M. et al. (1985) "A New Palladium-Catalyzed Synthesis of 1,2,3,4,4a,8b-Hexahydro-1,4-Methanobiphenylenes and 2-Phenylbicyclo[2.2.1]Hept-2enes*," Journal of Organometallic Chemistry 296:C11-C15.
Catellani, M. et al. (1996) "An Improved Synthesis of 1,4-cix,exo-Hexa- or Tetrahydromethano- or -ethanobiphenylene Derivatives Catalyzed by Palladium Complexes," Synthesis:769-772.
Catellani, M. et al. (2008) "Catalytic Sequential Reactions Involving Palladacycle-Directed Aryl Coupling Steps," Acc. Chem. Res. 41(11):1512-1522.
Chen, Z. et al. (2006) "Synthesis of a Novel Poly(iptycene) Ladder Polymer," Macromolecules 39(9):3202-3209.
Frye, C.L. et al. (1971) "So-called 'ladder structure' of equilibrated phenylsilsesquioxane," J. Am. Chem. Soc. 93(18):4599-4601.
Huang, D-J. et al. (1995) "[2+2] Dimerization of norbornadiene and its derivatives in the presence of nickel complexes and zinc metal," Journal of Organometallic Chemistry 490:C1-C7.
Kintzel, O. et al. (1996) "Synthesis of Model Compounds for the Structure Elucidation of a Ladder Polymer from Benzo[1,2-c: 4,5-c']difuran and a Diquinone Derivative," J. Org. Chem. 61(21):7304-7308.
Mannathan, S. et al. (2013) "Nickel-catalyzed regio- and diastereoselective intermolecular three-component coupling of oxabicyclic alkenes with alkynes and organoboronic acids," Chem. Commun. 49:1557-1559.

* cited by examiner

EFFICIENT SYNTHESIS OF RIGID LADDER POLYMERS

CROSS-REFERENCE TO RELATED APPLICATION

This application claims the benefit of U.S. Provisional Application No. 62/057,953, filed on Sep. 30, 2014, the disclosure of which is incorporated herein by reference in its entirety.

STATEMENT REGARDING FEDERALLY SPONSORED RESEARCH OR DEVELOPMENT

This invention was made with Government support under contract W911NF-14-1-0062 awarded by the Department of the Army. The Government has certain rights in the invention.

TECHNICAL FIELD

This disclosure generally relates to ladder polymers, the synthesis of ladder polymers, and their applications.

BACKGROUND

Rigid ladder polymers are promising materials for efficient gas separation, and their high rigidity is desirable for selectivity in gas separation. The synthesis of ladder polymers has been performed via Diels-Alder reactions, and based on Tröger's base formation and double aromatic nucleophilic substitution. Many of the synthetic methods still result in relatively flexible linkages in polymer backbones except for Tröger's base linkage. Additionally, the scope of ladder polymer structures is restricted by the few available synthetic methods, and often ladder polymers are formed with low yields.

It is against this background that a need arose to develop embodiments of this disclosure.

SUMMARY

One aspect of some embodiments of this disclosure relates to molecules with two-bond linkages by palladium or nickel-catalyzed annulation. Another aspect of some embodiments of this disclosure relates to the synthesis of molecules by palladium or nickel-catalyzed annulation.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

FIG. 8A: Thermal gravimetric analysis (TGA) analysis under argon indicates that the polymer was stable up to about 300° C., and lost about 14% by weight at about 515° C., which can be attributed to the loss of two methyl substituents. Upon further heating under argon, the polymer can be carbonized with nearly 81% mass retention at about 800° C. FIG. 8B: Brunauer-Emmett-Teller (BET) surface area analysis shows that frustrated packing of ladder chains resulted in a large intrinsic porosity of about 620 $m^2/g$.

DETAILED DESCRIPTION

Figure 1:
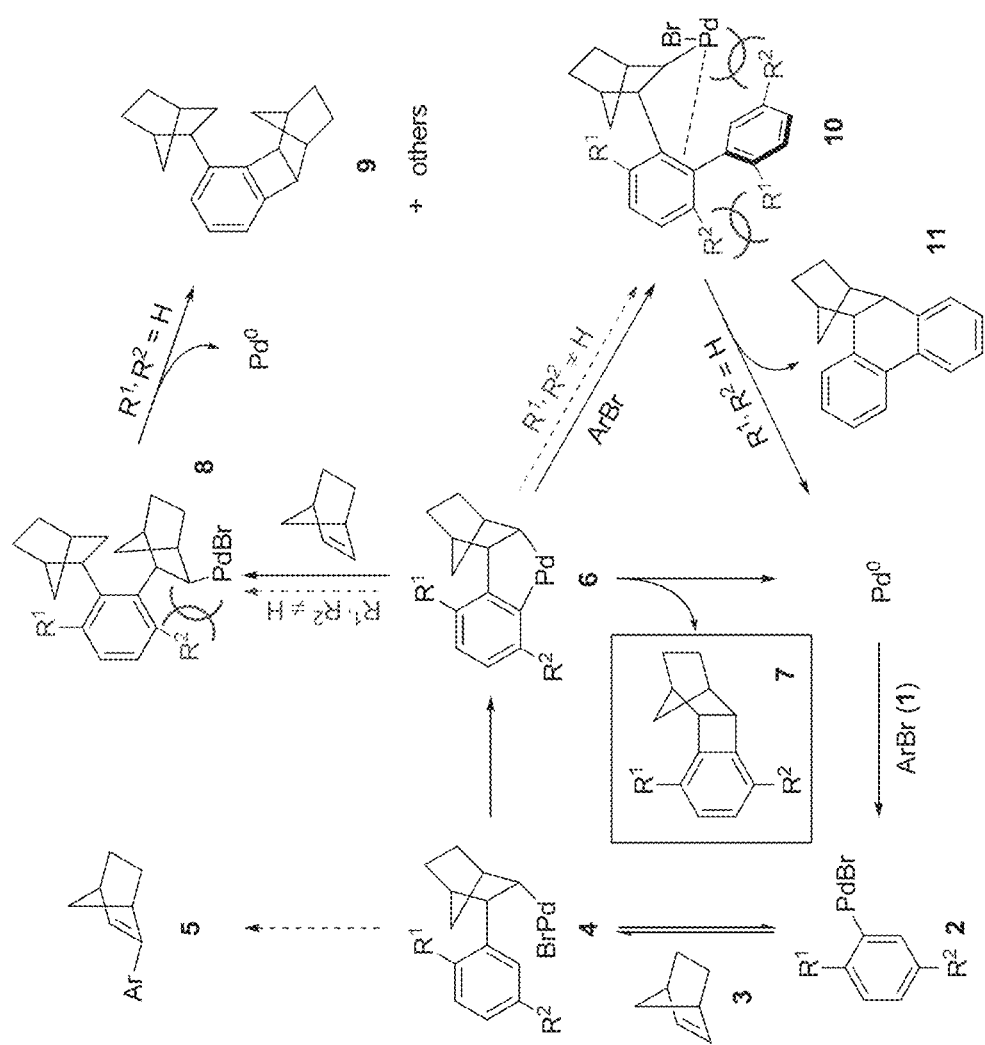
FIG. 1: A scheme showing potential products and selectivity by palladium-catalyzed annulation.

Embodiments of this disclosure are directed to molecules synthesized by formation of two-bond linkages between molecular building blocks. In some embodiments, the two-bond linkages are formed through palladium-catalyzed or nickel-catalyzed annulation reactions. In some embodiments, the formation of two-bond linkages leads to polymerization of molecular building blocks and yields ladder polymers having desirable properties, such as high rigidity and high porosity. Thus, some embodiments are directed to efficient methods to synthesize such rigid ladder polymer at high yields. Advantageously, embodiments of this disclosure provide a powerful and versatile palladium or nickel-catalyzed synthesis to yield improved ladder polymers with varied architectures.

Molecules with Two-Bond Linkages by Palladium or Nickel-Catalyzed Annulation In some embodiments, a molecule synthesized by formation of two-bond linkages includes at least one moiety represented by one of the following chemical formulas:

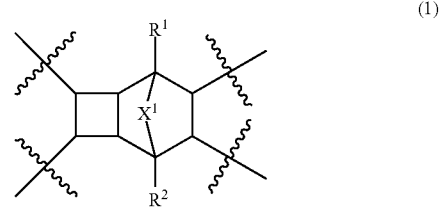

(1)

-continued

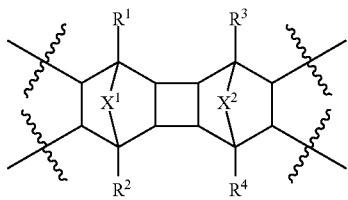
(2)

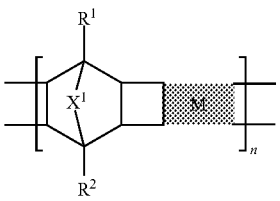
(3)

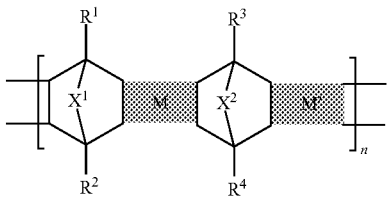
(4)

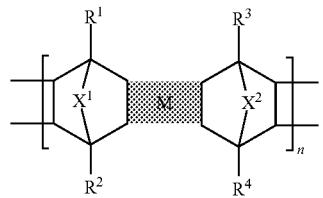
(5)

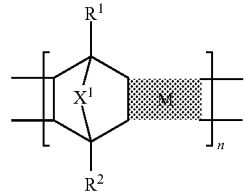
(6)

In formulas (1) and (2), $R^1$, $R^2$, $R^3$, and $R^4$ can be the same or different, and can be independently selected from substituents such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, —$OR^a$ (or other groups including a —O— moiety), —$O(CO)R^a$ (or other groups including a —O(CO)— moiety), —$O(CO)OR^a$ (or other groups including a —O(CO)O— moiety), —$O(CO)NR^aR^b$ (or other groups including a —O(CO)N< moiety), —$SR^a$ (or other groups including a —S— moiety), —$B(O)R^a(O)R^b$ (or other groups including a —B< moiety), —$NO_2$, —$NR^aR^b$ (or other groups including a —N< moiety), —$P(O)R^a(O)R^b$ (or other groups including a —P< moiety), —$PO(O)R^a(O)R^b$ (or other groups including a —(PO)< moiety), —CHO, —$(CO)R^a$ (or other groups including a —(CO)— moiety), —$(CO)OR^a$ (or other groups including a —(CO)O— moiety), —$(CO)NR^aR^b$ (or other groups including a —(CO)N< moiety), and —$Si(O)R^a(O)R^b(O)R^c$ (or other groups including a —Si≡ moiety); $X^1$ and $X^2$ can be the same or different, and can be independently selected from bridging moieties such as —[O]—, —[S]—, —[B(O)$R^d$]—, —[N$R^d$]—, —[P(O)$R^d$]—, —[(PO)(O)$R^d$]—, —[CO]—, —[C$R^dR^e$]—, —[C(O)$R^d$(O)$R^e$]—, —[Si(O)$R^d$(O)$R^e$]—, and other groups including at least one oxygen atom, at least one sulfur atom, at least one boron atom, at least one nitrogen atom, at least one phosphorus atom, or at least one carbon atom; and where $R^a$, $R^b$, $R^c$, $R^d$, and $R^e$ can be the same or different, and can be independently selected from substituents such hydride group, alkyl groups (including alkyl groups that are substituted and unsubstituted), aryl groups (including aryl groups that are substituted and unsubstituted), and heterocyclic groups (including heterocyclic groups that are substituted and unsubstituted). The moiety represented by formula (1) can be characterized as a cyclobutane group that is fused with a bicyclic group including the bridging moiety $X^1$ and which is substituted with $R^1$ and $R^2$; in some embodiments, at least one of, or each of, $R^1$ and $R^2$ can be different from a hydride group. The moiety represented by formula (2) can be characterized as a cyclobutane group that is fused between a pair of bicyclic groups, each including the bridging moiety $X^1$ (or $X^2$) and which is substituted with $R^1$ and $R^2$ (or $R^3$ and $R^4$); in some embodiments, at least one of, or at least two of, or at least three of, or each of, $R^1$, $R^2$, $R^3$, and $R^4$ can be different from a hydride group. A molecule synthesized by formation of two-bond linkages can include a single moiety represented by formula (1) or (2), or can include multiple instances (n instances corresponding to a degree of polymerization) of the moiety of formula (1) or (2) as repeat units, such as in the case of a ladder polymer.

In some embodiments, a molecule including at least one instance of the moiety of formula (1) or (2) is represented by one of the following chemical formulas:

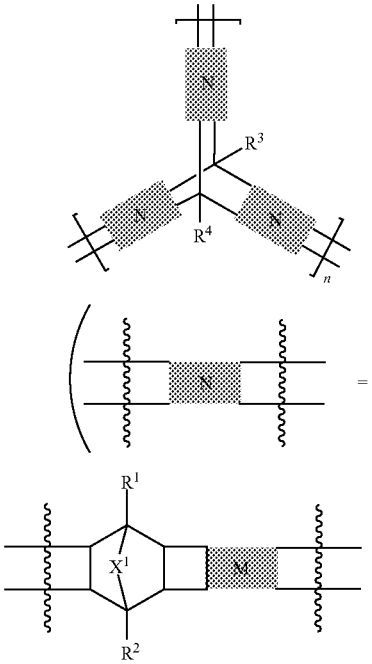
(7)

or

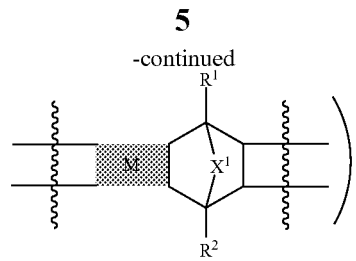

In formulas (3) through (7), $R^1$, $R^2$, $R^3$, and $R^4$ can be selected from substituents as explained above with reference to formulas (1) and (2), $X^1$ and $X^2$ can be selected from bridging moieties as explained above with reference to formulas (1) and (2), and n is the number of repeat units and is an integer that is 1 or greater than 1, such as 2 or greater, 3 or greater, 4 or greater, 5 or greater, 10 or greater, 20 or greater, 50 or greater, or 100 or greater. Moieties M and M' can be the same or different, and can be independently selected from aromatic groups (including aromatic groups that are substituted and unsubstituted, and that are monocyclic, bicyclic, tricyclic, and higher order polycyclic), and heterocyclic groups (including heterocyclic groups that are substituted and unsubstituted, and that are monocyclic, bicyclic, tricyclic, and higher order polycyclic). For example, M (and M') can be selected from groups represented by the following chemical formulas:

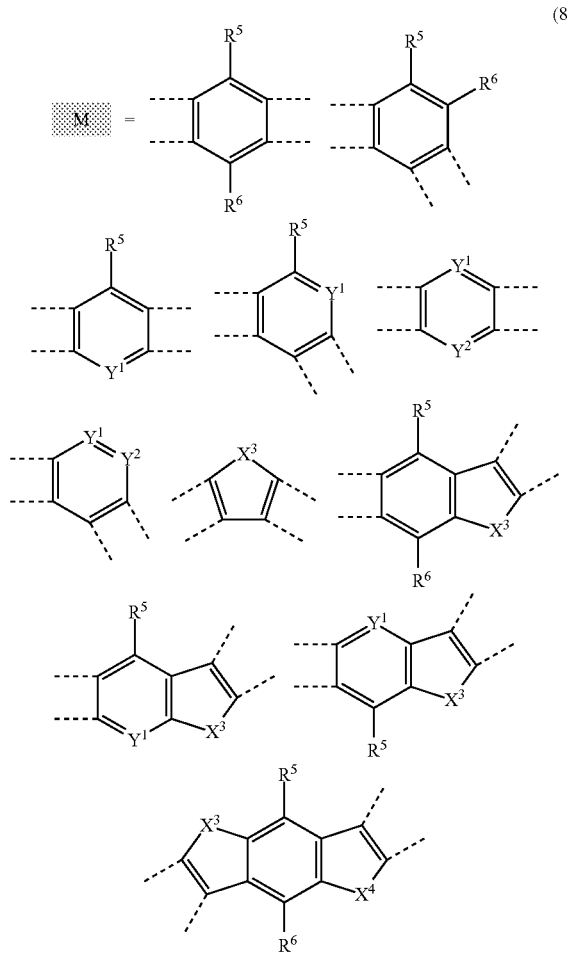

(8)

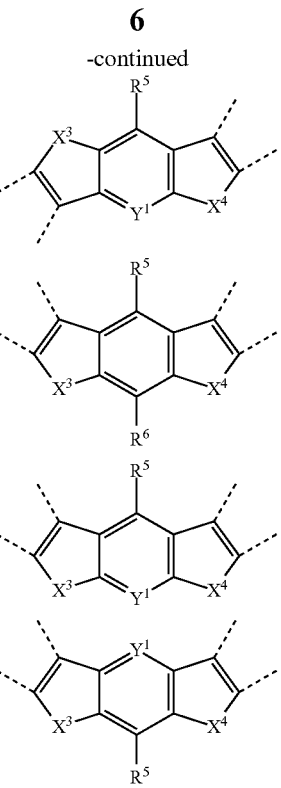

where $R^5$ and $R^6$ can be the same or different, and can be independently selected from substituents as explained above with reference to $R^1$, $R^2$, $R^3$, and $R^4$, such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, groups including a —O— moiety, groups including a —O(CO)— moiety, groups including a —O(CO)O— moiety), groups including a —O(CO)N< moiety, groups including a —S— moiety, groups including a —B< moiety, —NO$_2$, groups including a —N< moiety, groups including a —P< moiety, groups including a —PO< moiety, —CHO, groups including a —(CO)— moiety, groups including a —(CO)O— moiety, groups including a —(CO)N< moiety, and groups including a —Si≡ moiety; $X^3$ and $X^4$ can be the same or different, and can be independently selected from moieties such as —[O]—, —[S]—, —[B(O)R$^f$]—, —[NR$^f$]—, —[P(O)R$^f$]—, —[(PO)(O)R$^f$]—, —[CO]—, —[C(O)R$^f$(O)R$^g$]—, and —[Si(O)R$^f$(O)R$^g$]—; $Y^1$ and $Y^2$ can be the same or different, and can be independently from moieties such as —B═, —(CR$^h$)═, —N═, —P═, —C(O)R$^h$═, and —Si(O)R$^h$═; and where R$^f$, R$^g$, and R$^h$ can be the same or different, and can be independently selected from substituents such hydride group, alkyl groups (including alkyl groups that are substituted and unsubstituted), aryl groups (including aryl groups that are substituted and unsubstituted), and heterocyclic groups (including heterocyclic groups that are substituted and unsubstituted).

Additional examples of M (and M') include two or more cyclic moieties M$^a$ and M$^b$ that are directly fused with one another or indirectly fused through a linker moiety L, as represented by the connectivity in the following chemical formulas:

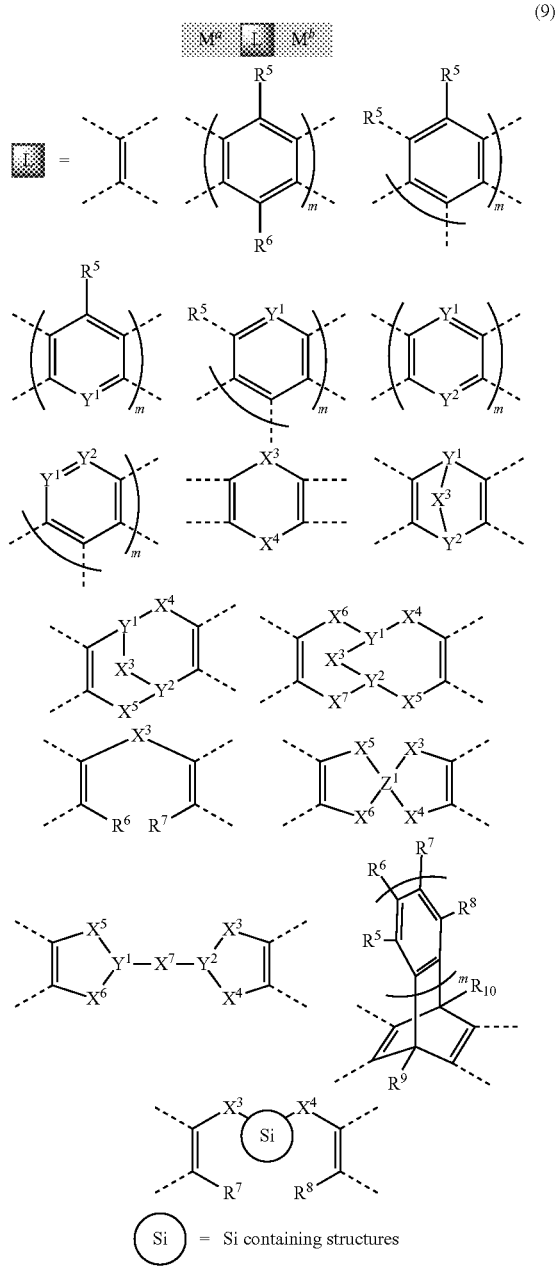

(9)

In formula (9), the cyclic moieties $M^a$ and $M^b$ can be the same or different, and can be independently selected from aromatic groups (including aromatic groups that are substituted and unsubstituted, and that are monocyclic, bicyclic, tricyclic, and higher order polycyclic), and heterocyclic groups (including heterocyclic groups that are substituted and unsubstituted, and that are monocyclic, bicyclic, tricyclic, and higher order polycyclic). For example, $M^a$ and $M^b$ can be independently selected from the groups of formula (8). $R^5$, $R^6$, $R^7$, $R^8$, $R^9$, and $R^{10}$ can be the same or different, and can be independently selected from substituents as explained above with reference to $R^1$, $R^2$, $R^3$, and $R^4$, such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, groups including a —O— moiety, groups including a —O(CO)— moiety, groups including a —O(CO)O— moiety), groups including a —O(CO)N< moiety, groups including a —S— moiety, groups including a —B< moiety, —NO$_2$, groups including a —N< moiety, groups including a —P< moiety, groups including a —PO< moiety, —CHO, groups including a —(CO)— moiety, groups including a —(CO)O— moiety, groups including a —(CO)N< moiety, and groups including a —Si≡ moiety; $X^3$, $X^4$, $X^5$, $X^6$, and $X^7$ can be the same or different, and can be independently selected from moieties such as —[O]—, —[S]—, —[B(O)R$^f$]—, —[CR$^f$R$^g$]$_p$— with p being 1 or greater than 1, —[NR$^f$]—, —[P(O)R$^f$]—, —[(PO)(O)R$^f$]—, —[CO]—, —[C(O)R$^f$(O)R$^g$]—, and —[Si(O)R$^f$(O)R$^g$]—; $Y^1$ and $Y^2$ can be the same or different, and can be independently from moieties such as —B=, —(CR$^h$)=, —N=, —P=, —C(O)R$^h$=, and —Si(O)R$^h$=; $Z^1$ is C or Si; m is an integer that is 1 or greater than 1, such as 2 or greater, 3 or greater, 4 or greater, 5 or greater, or 10 or greater; and where $R^f$, $R^g$, and $R^h$ can be the same or different, and can be independently selected from substituents such hydride group, alkyl groups (including alkyl groups that are substituted and unsubstituted), aryl groups (including aryl groups that are substituted and unsubstituted), and heterocyclic groups (including heterocyclic groups that are substituted and unsubstituted). The linker moiety L can be an acyclic or cyclic group including 2 or more carbon atoms and optionally including one or more heteroatoms, as, for example, shown in formula (9).

In some embodiments, a ladder polymer includes two or more of the same type of repeat units that are polymerized, such as two or more of the same type of repeat units of formulas (1) through (7). In some embodiments, the polymer includes two or more different types of repeat units that are polymerized, such as two or more different types of repeat units of formulas (1) through (7). In some embodiments, the polymer is a homopolymer, and, in some embodiments, the polymer is a copolymer. In some embodiments, the polymer is an alternating copolymer with regular alternating repeat units [1] and [2]. In some embodiments, the polymer is a periodic copolymer with repeat units [1] and [2] arranged in a repeating sequence, for example, as ([1]-[2]-[1]-[2]-[2]-[1]-[1]-[1]-[1]-[2]-[2]-[2])$_n$. In some embodiments, the polymer is a statistical copolymer in which the sequence of repeat units follows a statistical rule. If the probability of finding a given type repeat unit at a particular point in the polymer chain is substantially equal to a mole fraction of that repeat unit in the chain, then the polymer can be referred to as a random copolymer. In some embodiments, the polymer is a block copolymer including two or more homopolymer subunits linked by covalent bonds.

In some embodiments, a polymer includes at least one ladder subunit, which includes at least one instance of the repeat unit of formulas (1) through (7), and which is linked by covalent bonds to at least another non-ladder subunit, such as a homopolymer subunit corresponding to a polyester chain, a polyamide chain, a polyurethane chain, a polyvinyl chain, a polyether chain, a polysiloxane chain, or another type of polymer chain based on carbon-carbon links, carbon-oxygen links, silicon-oxygen links, carbon-nitrogen links, and hetero atom-hetero atom links.

In some embodiments, a polymer has a molecular weight (e.g., number average or mass average) that is about 4 kDa or more, about 6 kDa or more, about 8 kDa or more, about 10 kDa or more, about 20 kDa or more, about 30 kDa or more, about 40 kDa or more, about 50 kDa or more, about 60 kDa or more, about 70 kDa or more, about 80 kDa or more, about 90 kDa or more, or about 100 kDa or more. In some embodiments, a polymer has a polydispersity index that is about 4 or less, about 3.5 or less, about 3 or less, about 2.5 or less, about 2 or less, about 1.8 or less, about 1.6 or less, about 1.4 or less, about 1.3 or less, about 1.2 or less, or about 1.1 or less.

Synthesis of Molecules by Palladium or Nickel-Catalyzed Annulation

In some embodiments, a molecule, such as a ladder polymer, is synthesized by polymerizing or otherwise reacting at least one monomer (or molecular building block) A with at least one monomer (or molecular building block) B, as catalyzed by a palladium-containing catalyst, and in the presence of at least one ligand selected from phosphorus-containing organic ligands, nitrogen-containing organic ligands, and carbon-containing (or -based) ligands, and an organic or inorganic base in an organic solvent.

Monomer A can be selected from aromatic hydrocarbons (including aromatic hydrocarbons that are substituted with at least two X groups, and that are monocyclic, bicyclic, tricyclic, and higher order polycyclic), and heterocyclic compounds (including heterocyclic compounds that are substituted with at least two X groups, and that are monocyclic, bicyclic, tricyclic, and higher order polycyclic).

For example, monomer A can be an aromatic hydrocarbon or a heterocyclic compound that is monocyclic as represented by one of the following chemical formulas:

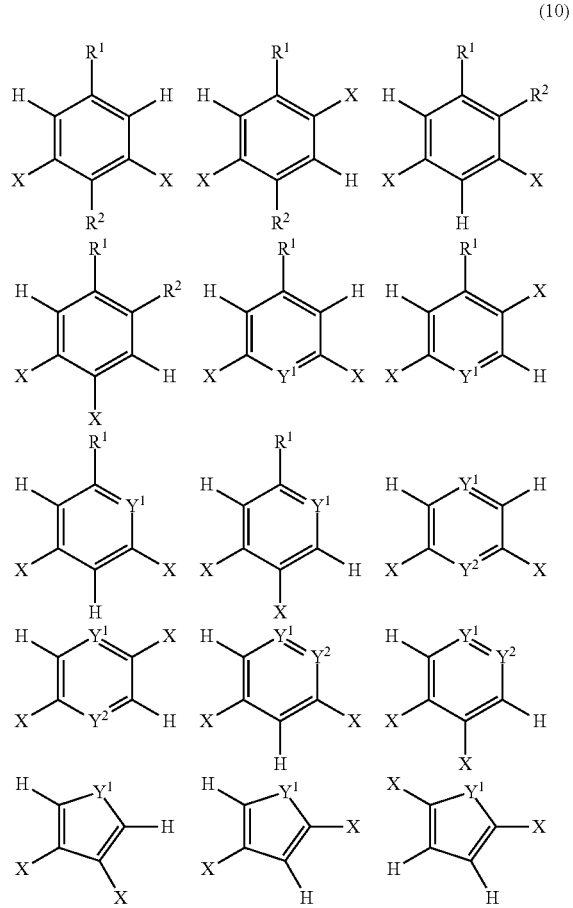

(10)

In formula (10), X is a halogen group or a sulfonate group, such as a trifluoromethanesulfonate group ($CF_3SO_3$—); two X's included per monomer A, in general, can be the same or different and can be selected from the aforementioned list; $R^1$ and $R^2$ can be the same or different, and can be independently selected from substituents such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, groups including a —O— moiety, groups including a —O(CO)— moiety, groups including a —O(CO)O— moiety), groups including a —O(CO)N< moiety, groups including a —S— moiety, groups including a —B< moiety, —$NO_2$, groups including a —N< moiety, groups including a —P< moiety, groups including a —PO< moiety, —CHO, groups including a —(CO)— moiety, groups including a —(CO)O— moiety, groups including a —(CO)N< moiety, and groups including a —Si≡ moiety; $X^1$ can be selected from moieties such as —[O]—, —[S]—, —[B(O)$R^a$]—, —[N$R^a$]—, —[P(O)$R^a$]—, —[(PO)(O)$R^a$]—, —[CO]—, —[C(O)$R^a$(O)$R^b$]—, and —[Si(O)$R^a$(O)$R^b$]—; $Y^1$ and $Y^2$ can be the same or different, and can be independently from moieties such as —B═, —(C$R^c$)═, —N═, —P═, —C(O)$R^c$═, and —Si(O)R═; and where $R^a$, $R^b$, and $R^c$ can be the same or different, and can be independently selected from substituents such hydride group, alkyl groups (including alkyl groups that are substituted and unsubstituted), aryl groups (including aryl groups that are substituted and unsubstituted), and heterocyclic groups (including heterocyclic groups that are substituted and unsubstituted). In some embodiments, at least one of, or each of, $R^1$ and $R^2$ can be different from a hydride group.

Additional examples of monomer A include two or more cyclic moieties $C^a$ and $C^b$ that are fused through a linker moiety L, as represented by the connectivity in the following chemical formula:

(11)

In formula (11), the cyclic moieties $C^a$ and $C^b$ can be the same or different, and can be independently selected from aromatic groups (including aromatic groups that are substituted with at least one X group, and that are monocyclic, bicyclic, tricyclic, and higher order polycyclic), and heterocyclic groups (including heterocyclic groups that are substituted with at least one X group, and that are monocyclic, bicyclic, tricyclic, and higher order polycyclic). For example, $C^a$ (and $C^b$) can be selected from groups represented by the following chemical formulas:

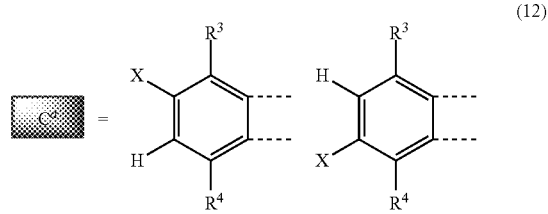

(12)

-continued

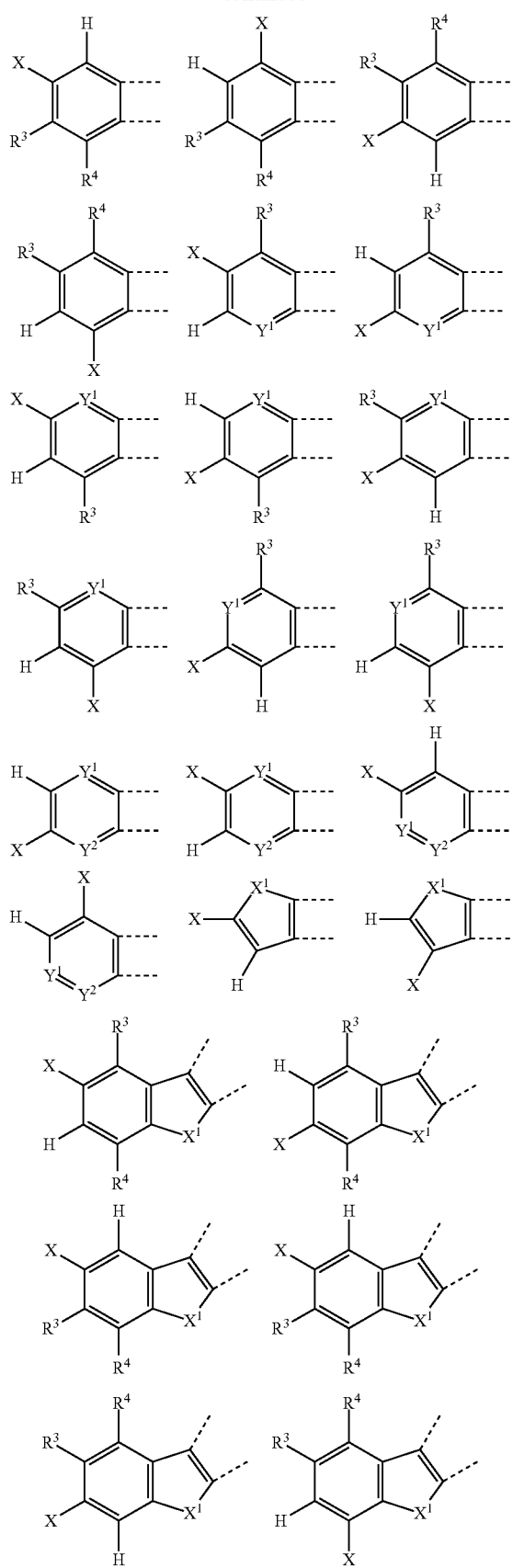

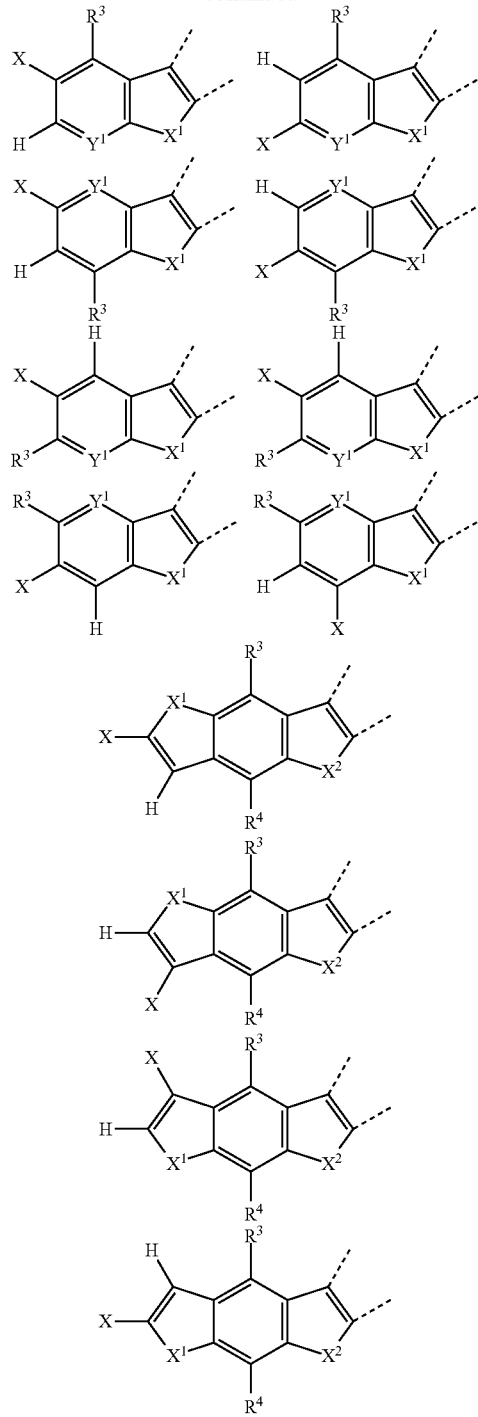

In formulas (11) and (12), X is a halogen group or a sulfonate group, such as a trifluoromethanesulfonate group ($CF_3SO_3$—); two X's included per monomer A, in general, can be the same or different and can be selected from the aforementioned list; $R^3$ and $R^4$ can be the same or different, and can be independently selected from substituents such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, groups including a —O— moiety, groups including a —O(CO)— moiety, groups including a —O(CO)O— moiety), groups including a —O(CO)N< moiety, groups including a —S— moiety, groups including a —B< moiety, —NO$_2$, groups including a —N< moiety, groups including a —P< moiety, groups including a —PO< moiety, —CHO, groups including a —(CO)— moiety, groups including a —(CO)O— moiety, groups including a —(CO)N< moiety, and groups including a —Si≡ moiety; X$^1$ and X$^2$ can be the same or different, and can be independently selected from moieties such as —[O]—, —[S]—, —[B(O)R$^a$]—, —[NR$^a$]—, —[P(O)R$^a$]—, —[(PO)(O)R$^a$]—, —[CO]—, —[C(O)R$^a$(O)R$^b$]—, and —[Si(O)R$^a$(O)R$^b$]—; Y$^1$ and Y$^2$ can be the same or different, and can be independently from moieties such as —B≡, —(CR$^c$)≡, —N≡, —P≡, —C(O)R$^c$≡, and —Si(O)R$^c$≡; the linker moiety L can be an acyclic or cyclic group including 2 or more carbon atoms and optionally including one or more heteroatoms, as, for example, selected from the groups of formula (9); and where R$^a$, R$^b$, and R$^c$ can be the same or different, and can be independently selected from substituents such hydride group, alkyl groups (including alkyl groups that are substituted and unsubstituted), aryl groups (including aryl groups that are substituted and unsubstituted), and heterocyclic groups (including heterocyclic groups that are substituted and unsubstituted).

Monomer B can be selected from polycyclic compounds including at least two carbon-carbon double bonds per molecule and at least one bridging moiety per molecule. For example, monomer B can be a bicyclic compound or a higher order polycyclic compound as represented by one of the following chemical formulas:

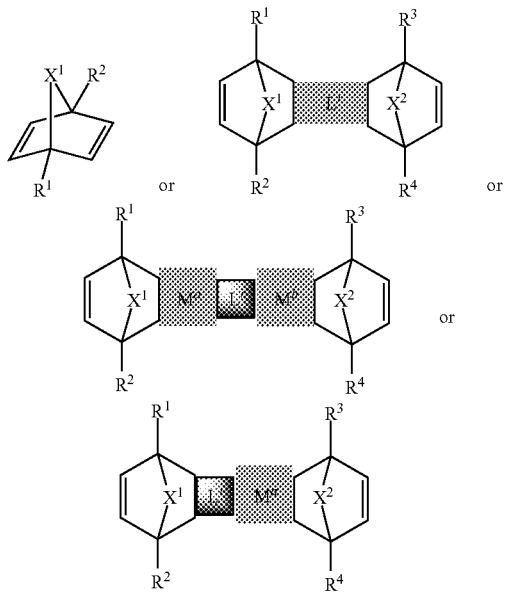

(13)

In formula (13), R$^1$, R$^2$, R$^3$, and R$^4$ can be the same or different, and can be independently selected from substituents such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, groups including a —O— moiety, groups including a —O(CO)— moiety, groups including a —O(CO)O— moiety), groups including a —O(CO)N< moiety, groups including a —S— moiety, groups including a —B< moiety, —NO$_2$, groups including a —N< moiety, groups including a —P< moiety, groups including a —PO< moiety, —CHO, groups including a —(CO)— moiety, groups including a —(CO)O— moiety, groups including a —(CO)N< moiety, and groups including a —Si≡ moiety; X$^1$ and X$^2$ can be the same or different, and can be independently selected from moieties such as —[O]—, —[S]—, —[B(O)R$^a$]—, —[NR$^a$]—, —[P(O)R$^a$]—, —[(PO)(O)R$^a$]—, —[CO]—, —[CR$^a$R$^b$]—, —[C(O)R$^a$(O)R$^b$]—, and —[Si(O)R$^a$(O)R$^b$]—; and where R$^a$ and R$^b$ can be the same or different, and can be independently selected from substituents such hydride group, alkyl groups (including alkyl groups that are substituted and unsubstituted), aryl groups (including aryl groups that are substituted and unsubstituted), and heterocyclic groups (including heterocyclic groups that are substituted and unsubstituted). M$^a$ and M$^b$ are cyclic moieties that can be the same or different, and can be independently selected from aromatic groups (including aromatic groups that are substituted and unsubstituted, and that are monocyclic, bicyclic, tricyclic, and higher order polycyclic), and heterocyclic groups (including heterocyclic groups that are substituted and unsubstituted, and that are monocyclic, bicyclic, tricyclic, and higher order polycyclic). For example, M$^a$ and M$^b$ can be independently selected from the groups of formula (8). The linker moiety L' can be an acyclic or cyclic group including 2 or more carbon atoms and optionally including one or more heteroatoms, as, for example, selected from

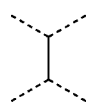

and the groups of formula (9).

In some embodiments, a molecule, such as a ladder polymer, is synthesized by polymerizing or otherwise reacting one or more monomers (or molecular building blocks) AB, as catalyzed by a palladium-containing catalyst, and in the presence of at least one ligand selected from phosphorus-containing organic ligands, nitrogen-containing organic ligands, and carbon-containing (or -based) ligands, and an organic or inorganic base in an organic solvent.

Monomer AB can be selected from polycyclic compounds including at least one aromatic group (an aromatic group that is substituted with at least one X group, and that is monocyclic, bicyclic, tricyclic, or higher order polycyclic) or at least one heterocyclic group (a heterocyclic group that is substituted with at least one X group, and that is monocyclic, bicyclic, tricyclic, or higher order polycyclic) that is directly or indirectly fused with a bicyclic group including a bridging moiety and at least one carbon-carbon double bond.

For example, monomer AB can be represented by the following chemical formula:

(14)

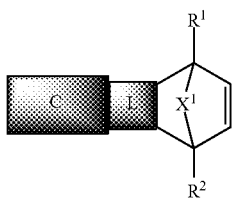

In formula (14), $R^1$ and $R^2$ can be the same or different, and can be independently selected from substituents such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, groups including a —O— moiety, groups including a —O(CO)— moiety, groups including a —O(CO)O— moiety), groups including a —O(CO)N< moiety, groups including a —S— moiety, groups including a —B< moiety, —$NO_2$, groups including a —N< moiety, groups including a —P< moiety, groups including a —PO< moiety, —CHO, groups including a —(CO)— moiety, groups including a —(CO)O— moiety, groups including a —(CO)N< moiety, and groups including a —Si≡ moiety; $X^1$ can be selected from moieties such as —[O]—, —[S]—, —[B(O)$R^a$]—, —[$NR^a$]—, —[P(O)$R^a$]—, —[(PO)(O)$R^a$]—, —[CO]—, —[$CR^aR^b$]—, —[C(O)$R^a$(O)$R^b$]—, and —[Si(O)$R^a$(O)$R^b$]—; and where $R^a$ and $R^b$ can be the same or different, and can be independently selected from substituents such hydride group, alkyl groups (including alkyl groups that are substituted and unsubstituted), aryl groups (including aryl groups that are substituted and unsubstituted), and heterocyclic groups (including heterocyclic groups that are substituted and unsubstituted). C is a cyclic moiety that can be selected from aromatic groups (including aromatic groups that are substituted with at least one X group, and that are monocyclic, bicyclic, tricyclic, and higher order polycyclic), and heterocyclic groups (including heterocyclic groups that are substituted with at least one X group, and that are monocyclic, bicyclic, tricyclic, and higher order polycyclic). For example, C can be selected from the groups formula (12). The linker moiety L can be an acyclic or cyclic group including 2 or more carbon atoms and optionally including one or more heteroatoms, as, for example, selected from the groups of formula (9).

In some embodiments, a molecule, such as a ladder polymer, is synthesized by polymerizing or otherwise reacting one or more monomers (or molecular building blocks) C, as catalyzed by a nickel-containing catalyst, and in the presence of at least one ligand selected from phosphorus-containing organic ligands, nitrogen-containing organic ligands, and carbon-containing (or -based) ligands in an organic solvent. An organic or inorganic base can be included or may not be omitted, and, depending on the form of the nickel-containing catalyst (oxidation state of nickel), a reducing agent, such as zinc, can be included to activate the catalyst.

Monomer C can be selected from polycyclic compounds including at least two carbon-carbon double bonds per molecule and at least two bridging moieties per molecule. For example, monomer C can be a polycyclic compound as represented by one of the following chemical formulas:

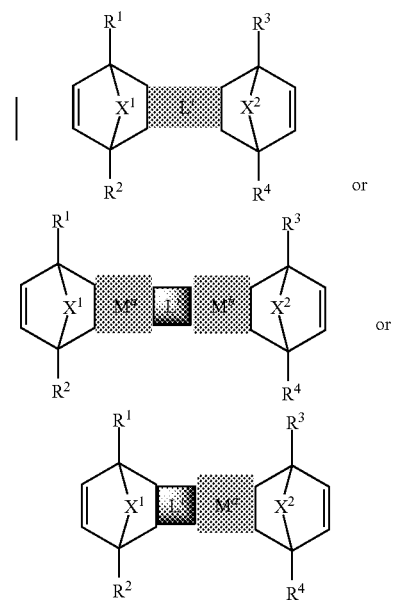

(15)

In formula (15), $R^1$, $R^2$, $R^3$, and $R^4$ can be the same or different, and can be independently selected from substituents such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, groups including a —O— moiety, groups including a —O(CO)— moiety, groups including a —O(CO)O— moiety), groups including a —O(CO)N< moiety, groups including a —S— moiety, groups including a —B< moiety, —$NO_2$, groups including a —N< moiety, groups including a —P< moiety, groups including a —PO< moiety, —CHO, groups including a —(CO)— moiety, groups including a —(CO)O— moiety, groups including a —(CO)N< moiety, and groups including a —Si≡ moiety; $X^1$ and $X^2$ can be the same or different, and can be independently selected from moieties such as —[O]—, —[S]—, —[B(O)$R^a$]—, —[$NR^a$]—, —[P(O)$R^a$]—, —[(PO)(O)$R^a$]—, —[CO]—, —[$CR^aR^b$]—, —[C(O)$R^a$(O)$R^b$]—, and —[Si(O)$R^a$(O)$R^b$]—; and where $R^a$ and $R^b$ can be the same or different, and can be independently selected from substituents such hydride group, alkyl groups (including alkyl groups that are substituted and unsubstituted), aryl groups (including aryl groups that are substituted and unsubstituted), and heterocyclic groups (including heterocyclic groups that are substituted and unsubstituted). $M^a$ and $M^b$ are cyclic moieties that can be the same or different, and can be independently selected from aromatic groups (including aromatic groups that are substituted and unsubstituted, and that are monocyclic, bicyclic, tricyclic, and higher order polycyclic), and heterocyclic groups (including heterocyclic groups that are substituted and unsubstituted, and that are monocyclic, bicyclic, tricyclic, and higher order polycyclic). For example, $M^a$ and $M^b$ can be independently selected from the groups of formula (8). The linker moiety L' can be an acyclic or cyclic group including 2 or more carbon atoms and optionally including one or more heteroatoms, as, for example, selected from

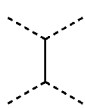

and the groups of formula (9).

In some embodiments, methods for synthesizing a molecule, such as a ladder polymer, include reacting monomers in the presence of at least one ligand selected from phosphorus-containing organic ligands, nitrogen-containing organic ligands, and carbon-containing (or -based) ligands. Examples of suitable ligands include phosphines, N-heterocyclic carbine (NHC), or a combination thereof. A phosphine ligand can be represented by the formula: PRR'R" or RR'PAPR"R'", and the NHC ligand can be represented by the formula:

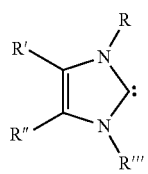

(16)

and where R, R', R", and R'" can be the same or different, and can be independently selected from substituents such as hydride group, alkyl groups (including alkyl groups that are substituted and unsubstituted), aryl groups (including aryl groups that are substituted and unsubstituted), heterocyclic groups (including heterocyclic groups that are substituted and unsubstituted), halogen groups, groups including a —O— moiety, groups including a —O(CO)— moiety, groups including a —O(CO)O— moiety), groups including a —O(CO)N< moiety, groups including a —S— moiety, groups including a —B< moiety, —NO$_2$, groups including a —N< moiety, groups including a —P< moiety, groups including a —PO< moiety, —CHO, groups including a —(CO)— moiety, groups including a —(CO)O— moiety, groups including a —(CO)N< moiety, and groups including a —Si≡ moiety; and A is a bivalent, saturated or unsaturated hydrocarbon group, which can be substituted or unsubstituted.

In some embodiments, methods for synthesizing a molecule, such as a ladder polymer, include reacting monomers in the presence of a metal catalyst. In some embodiments, the metal catalyst is a transition metal catalyst. In some embodiments, the transition metal catalyst is a palladium-containing catalyst, and, in some embodiments, the transition metal catalyst is a nickel-containing catalyst. Palladium can be in various forms of Pd(0) (elemental form) or Pd(II), such as palladium-containing organic complexes. Nickel can be in various forms of Ni(0) (elemental nickel) or Ni(II), such as such as nickel-containing organic complexes. In some embodiments, the metal catalyst is another transition metal catalyst or a combination of different transition metal catalysts, such as selected from Groups 3, 4, 5, 6, 7, 8, 9, 10, 11, and 12 of the Periodic Table.

In some embodiments, methods for synthesizing a molecule, such as a ladder polymer, include reacting monomers in the presence of an organic or inorganic base. The base can be any suitable base for use in palladium-catalyzed or nickel-catalyzed annulation reactions. Examples of suitable bases include aprotic bases such as cesium carbonate ($Cs_2CO_3$), potassium carbonate ($K_2CO_3$), sodium carbonate ($Na_2CO_3$), sodium fluoride (NaF), potassium fluoride (KF), or combinations thereof. Protic bases, such as sodium hydroxide (NaOH), potassium hydroxide (KOH), or combinations thereof, also can be suitable bases, for example, if there are little or no hydrolysable groups (e.g., —CN) in the monomers.

In some embodiments, methods for synthesizing a molecule, such as a ladder polymer, include reacting monomers in the presence of a reducing agent. The reducing agent can serve to activate a metal catalyst by reducing a metal from its (II) form to its elemental (0) form, such as Ni(II) to Ni (0). Examples of suitable reducing agents include zinc, among other elemental and compound reducing agents.

In some embodiments, methods for synthesizing a molecule, such as a ladder polymer, include reacting monomers in an inert atmosphere. The inert atmosphere can include inert gases such as argon, nitrogen, or combinations thereof.

In some embodiments, methods for synthesizing a molecule, such as a ladder polymer, include reacting monomers in a solvent, such as an organic solvent. The solvent can be dried to reduce water content and can be degassed to reduce oxygen content. In some embodiments, the solvent is a non-polar organic solvent, such as benzene, alkylbenzenes (e.g., toluene, xylene, and mesitylene), long-chain hydrocarbons (e.g., octane), ethyl acetate, or combinations thereof. In some embodiments, the solvent is an aprotic polar organic solvent, such as N,N-dimethylacetamide (DMAc), N'N-dimethylformamide (DMF), dimethylsulfoxide (DMSO), N-methylpyrrolidinone (NMP), sulfolane, diphenylsulfone, or combinations thereof. In some embodiments, a non-polar solvent is used in addition to an aprotic polar solvent. The non-polar solvent can serve to solubilize a resulting polymer and also can serve to solubilize the monomers in the aprotic polar solvent during the reaction.

In some embodiments, methods for synthesizing a molecule, such as a ladder polymer, include reacting monomers at an elevated temperature for a period of time suitable to enhance yield. The temperature can be, for example, in a range from about 15-200° C. In some embodiments, the temperature can be about 25° C. to about 150° C. In some embodiments, the temperature can be in a range of about 50-140° C., such as about 60-140° C., about 80-140° C., or about 100-130° C., which can reduce the period of time for synthesizing ladder polymers. In some embodiments, the polymerization period of time can be, for example, from less than about 1 hour to as long as about 72 hours. In some embodiments, the temperature of the polymerization is about 60° C., about 70° C., about 80° C., about 90° C., about 95° C., about 100° C., about 105° C., about 110° C., about 115° C., about 120° C., about 125° C., about 130° C., about 135° C., or about 140° C. In some embodiments, the temperature of the polymerization is about 115° C.

In some embodiments, conversion of monomers to polymers can be attained at yields greater than about 80%. In some embodiments, conversion of monomers to polymers can be about 85% or greater, about 90% or greater, about 95% or greater, about 96% or greater, about 97% or greater, about 98% or greater, or about 99% or greater. In some embodiments, conversion of monomers to polymers is substantially quantitative (e.g., near 100%).

Applications

Figure 7:
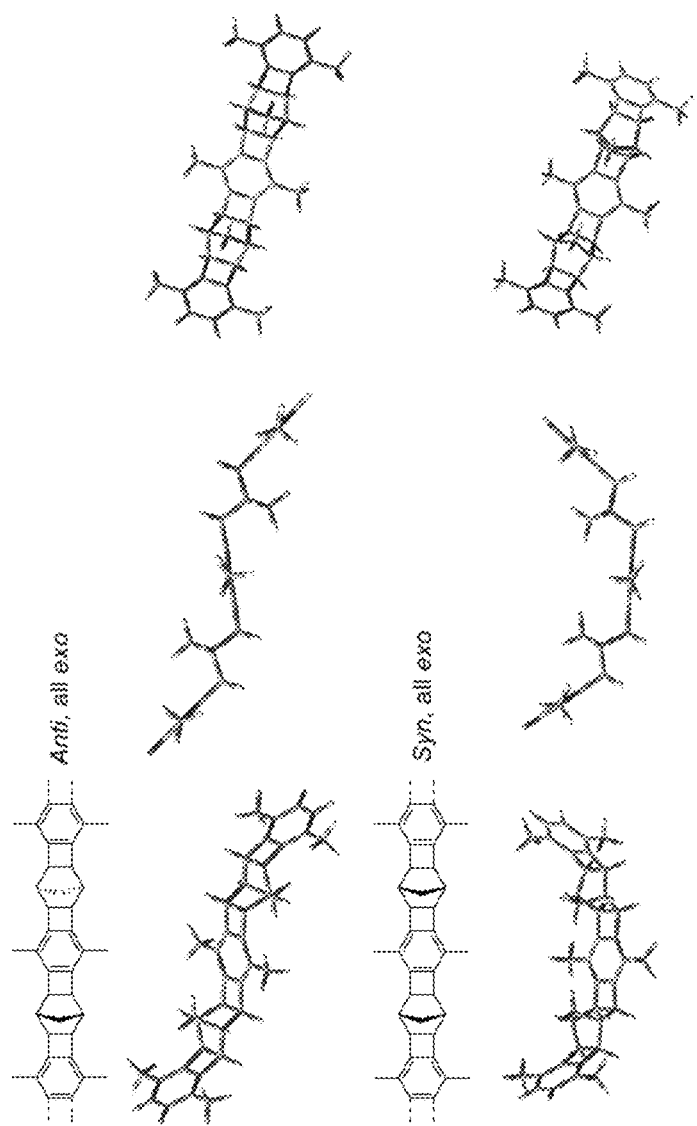
FIG. 7: Rigid conformation of ladder polymers, showing calculated structures of a segment of the ladder polymer (repeat unit). Two conformational isomers are possible in the ladder polymers. Both conformations can result in rigid backbones.

In some embodiments, a ladder polymer (or a ladder subunit of a polymer) has a kinked, rigid, and non-conjugated structure. In some embodiments, the polymer has a high degree of unsaturation, for example, where a mole ratio of hydrogen to carbon in the polymer is about 1.5 or less, about 1.4 or less, about 1.3 or less, about 1.2 of less, about 1.1 or less, about 1 or less, or about 0.9 or less, and has a frustrated chain packing with high intrinsic porosity, such as resulting from the presence of bicyclic groups including bridging moieties. In some embodiments, the polymer has a high porosity, as characterized by a Brunauer-Emmett-Teller (BET) surface area of about 300 $m^2/g$ or more, about 400 $m^2/g$ or more, about 500 $m^2/g$ or more, about 600 $m^2/g$ or more, or about 620 $m^2/g$ or more, and up to about 1000 $m^2/g$ or more. In some embodiments, the polymer has no detectable phase transition from about 25° C. up to about 200° C. In some embodiments, at least two conformational isomers can exist in the polymer, namely anti, all exo, and syn, all exo. (FIG. 7). Both conformations result in a rigid backbone of the polymer. In some embodiments, the polymer has high thermostability, and can operate at various extreme temperatures.

Polymers of embodiments of this disclosure are useful as materials for a number of applications, including as porous materials for separation of gases, liquids, and molecules dissolved in a solvent (in the form of membranes or solid monolithic structures); porous materials as adsorbents and for catalysis; low dielectric materials; carbon fiber precursors or reinforced fibers; thermal conductors; gas storage materials; porous supports; photoresist components; coatings; packaging materials; liquid crystal motifs; plastic additives; and rheological modifiers.

In some embodiments, a polymer can be used as a soluble porous material. In some embodiments, the soluble porous material can be used for gas separation or liquid separation, or as adsorbents or for catalysis. The polymer can be cast in a number of suitable forms, for example, as free-standing membranes, dense films, coated films, coatings, membranes on support materials (e.g., thin film composite membranes), beads, or powders.

In some embodiments, a polymer can be used as a low dielectric material. Dielectric constant relates to the permittivity of a material when polarized in response to an applied field. The greater the polarization developed by a material in an applied field of given strength, the greater is the dielectric constant. The polymer of some embodiments has a low dielectric constant (e.g., < about 4), along with a high porosity. In some embodiments, the polymer is a porous dielectric material that has a dielectric constant in the range of about 1.5 to about 3. In some embodiments, the polymer is a porous dielectric material that has an average pore size that is less than about 50 nm, such as in a range of about 1 nm to about 10 nm.

In some embodiments, a polymer can be used as a carbon fiber precursor or can be included in reinforced fibers to form fiber-reinforced materials. In some embodiments, the polymer can be used as, or can be included in, a carbon fiber precursor, a reinforced fiber, or an activated carbon material with a high surface area, a high porosity, and a high electric conductivity that can be used as a conductor or an electrode material of a supercapacitor.

In some embodiments, a polymer has a high thermal conductivity and can be used as a thermal conductor. In some embodiments, the polymer can be used to conduct and dissipate heat rapidly. In some embodiments, heat transfer occurs at a faster rate across the polymer of high thermal conductivity than across other materials of lower thermal conductivity.

In some embodiments, a polymer of high thermal conductivity can be used in various industrial settings, such as heat sink applications. In some embodiments, the polymer can be used as a thermal conductor in a number of electronic products, such as for chip cooling in a smart phone. The high thermal conductivity of the polymer can be widely applied to, for example, high power light-emitting diodes (LEDs), smart mobile-phones, LED panels, tablet and laptop computers.

EXAMPLES

The following examples describe specific aspects of some embodiments of this disclosure to illustrate and provide a description for those of ordinary skill in the art. The examples should not be construed as limiting this disclosure, as the examples merely provide specific methodology useful in understanding and practicing some embodiments of this disclosure.

Example 1

Efficient Synthesis of Rigid Ladder Polymers Via Palladium-Catalyzed Annulation

Transition metal catalysis has stimulated the emergence of new polymer chemistry to gain access to new polymers and new materials since the discovery of Ziegler-Natta catalyst. Some of the more recent examples of polymer chemistry developed based on transition metal catalysis include olefin metathesis polymerizations, atom transfer radical polymerization, conjugated polymer synthesis by cross-coupling reactions, and stereo-selective ring-opening polymerizations.

A palladium-catalyzed reaction between aryl bromides and norbornene (NB) has been developed (FIG. 1). The reaction is initiated with oxidative addition of Pd(0) species to aryl halide 1 to form Pd(II) species 2, followed by NB insertion to form complex 4, which yields both the Heck product 5 and palladacycle 6 from C—H activation on the arene. Palladacycle 6 further underwent reductive elimination to form an interesting benzocyclobutene (BCB) product 7. Other reaction pathways are possible, leading to products 9 and 11 as shown in FIG. 1.

Although the reaction is not highly selective, the BCB product can act as a motif to synthesize rigid ladder polymers with little or no rotational freedom. In ladder polymers, repeat units are connected by two bonds instead of one bond in other polymers. Therefore, ladder polymers have more restricted chain conformations and improved stability.

Figure 2:
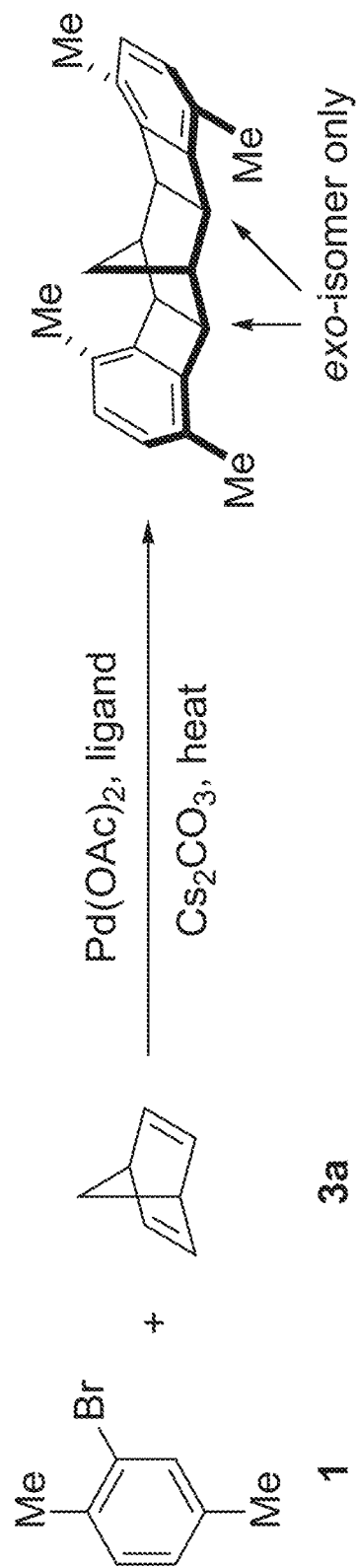
FIG. 2: Optimization of a model reaction for ladder polymerization.
Figure 5:
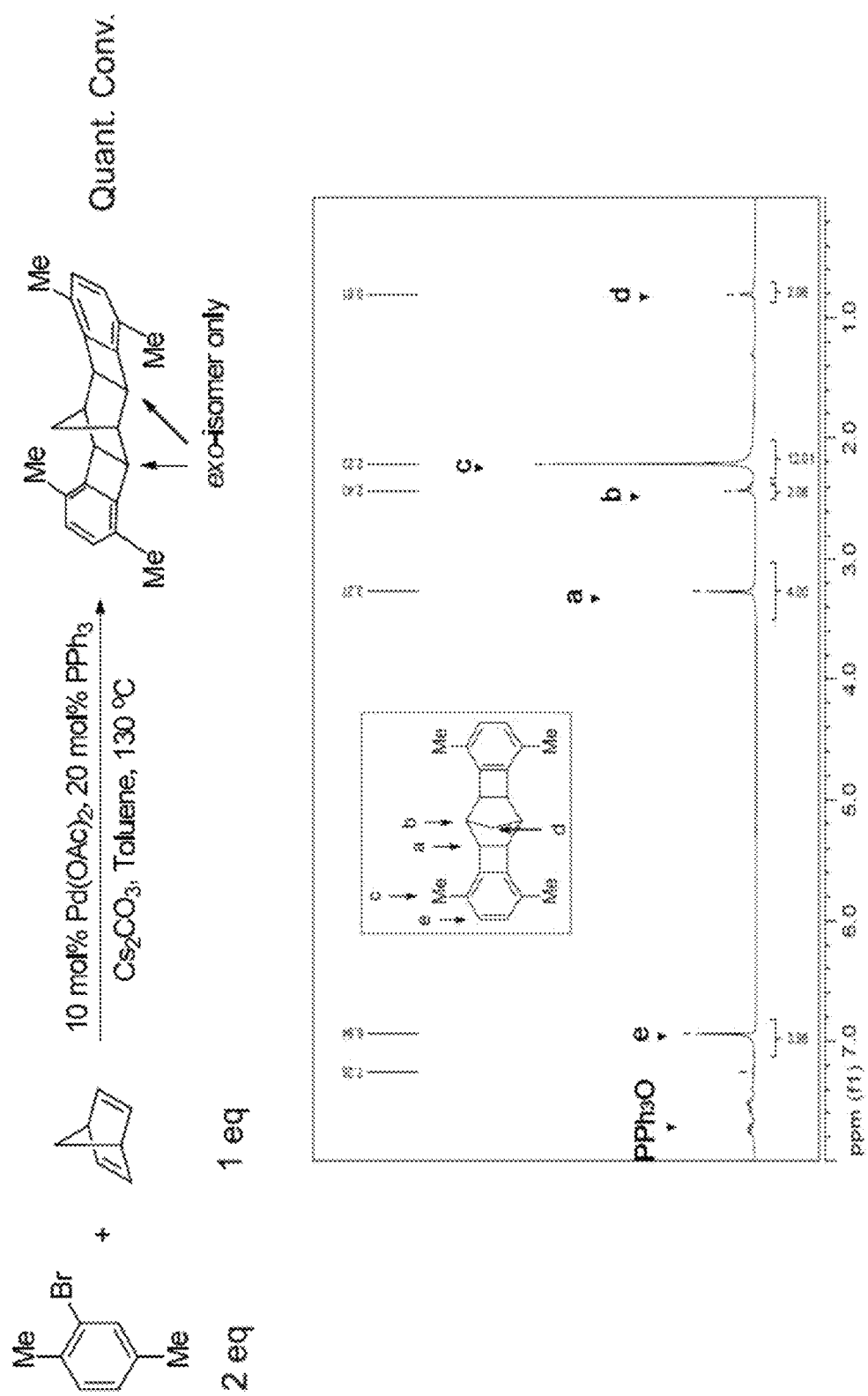
FIG. 5: Example of palladium-catalyzed small molecule model reaction for ladder polymerization. $^1$H NMR spectrum of a crude reaction mixture of the model reaction in $CDCl_3$, showing clean and quantitative conversion to form a ladder linkage in a model substrate.

In this example, the catalytic synthesis of ladder polymers in quantitative yields using optimized annulation reaction from readily available building blocks is reported. A model reaction between 2-bromotoluene and norbornadiene (NBD) using about 10 mol % $Pd(PPh_3)_4$ and $K_2CO_3$ resulted in substantially complete conversion of starting materials but also complex by-products. Blocking one ortho and one meta positions of the aryl halide is proposed to inhibit the reaction pathways of products 9 and 10 (FIG. 1) due to steric congestion and selectively yield the desired BCB product. After initial optimization, a clean BCB product was formed in quantitative yield after starting the reaction with 2-bromo-1,4-dimethylbenzene and NBD, and using $Pd(OAc)_2$, $PPh_3$, and $Cs_2CO_3$ at about 130° C., and the reaction was highly regioselective to select the exo-isomer (Table 1 and FIGS. 2 and 5). The reaction was sensitive to the steric hindrance of the phosphine ligand, as bulkier ligands gave lower yields. N-heterocyclic carbene (NHC) also gave lower yields of product.

TABLE 1

Optimization of a Model Reaction for Ladder Polymerization[a]

| Entry | Ligand | Temp. (° C.) | cat. (mol %)[b] | Conv. (%)[c] |
|---|---|---|---|---|
| 1 | PPh$_3$ | 130 | 5 | quant.[h] |
| 2 | PCy$_3$ | 130 | 5 | 94 |
| 3 | PtBu$_3$ | 130 | 5 | 68 |
| 4 | P(o-Tol)$_3$ | 130 | 5 | <5 |
| 5 | NHC[d] | 130 | 5 | <5[e] |
| 6 | PPh$_3$ | 115 | 5 | quant. |
| 7 | PPh$_3$ | 100 | 5 | 80 |
| 8 | PPh$_3$ | 115 | 1 | quant. |
| 9[f] | PPh$_3$ | 115 | 0.1 | 91 |
| 10[g] | PPh$_3$ | 115 | 0.1 | quant. |

[a]Reactions were performed using Pd(OAc)$_2$, 2 eq. ligand, Cs$_2$CO$_3$, at [substrate] = about 0.1M in toluene for about 5 hours in a sealed tube, unless otherwise noted.
[b]Based on the mole ratio of Pd to halide.
[c]Determined by $^1$H NMR of crude reaction mixture.
[d]PEPPSI-IPr Pd catalyst was used.
[e]Heck product was obtained.
[f]Reaction run for about 24 hours.
[g]Reaction run in THF for about 24 hours.
[h]quant. Means quantitative.
Abbreviations:
OAc = acetate;
Ph = phenyl;
Cy = cyclohexyl;
tBu = t-butyl;
o-Tol = o-tolyl.

Quantitative yield of a desired product could still be obtained when the catalyst loading was lowered to about 1 mol % and the reaction temperature was lowered to about 115° C. Further lowering the catalyst loading or temperature slowed the reaction, yet still yielded a clean product. Indeed, about 91% and quantitative yields in toluene and tetrahydrofuran (THF) were obtained, respectively, when using about 0.1 mol % catalyst loading and about 115° C. after about 24 hours. The turnover number (TON) was measured to be about 1176, and turnover frequency (TOF) was measured to be about 49 h$^{-1}$ in toluene. This represents two orders of magnitude reduction in catalyst loading as compared to similar annulation reactions using other substrates and other catalytic systems. This low catalyst loading and clean chemistry allow for the application of this annulation reaction to polymer chemistry and scalable materials synthesis.

Figure 3:
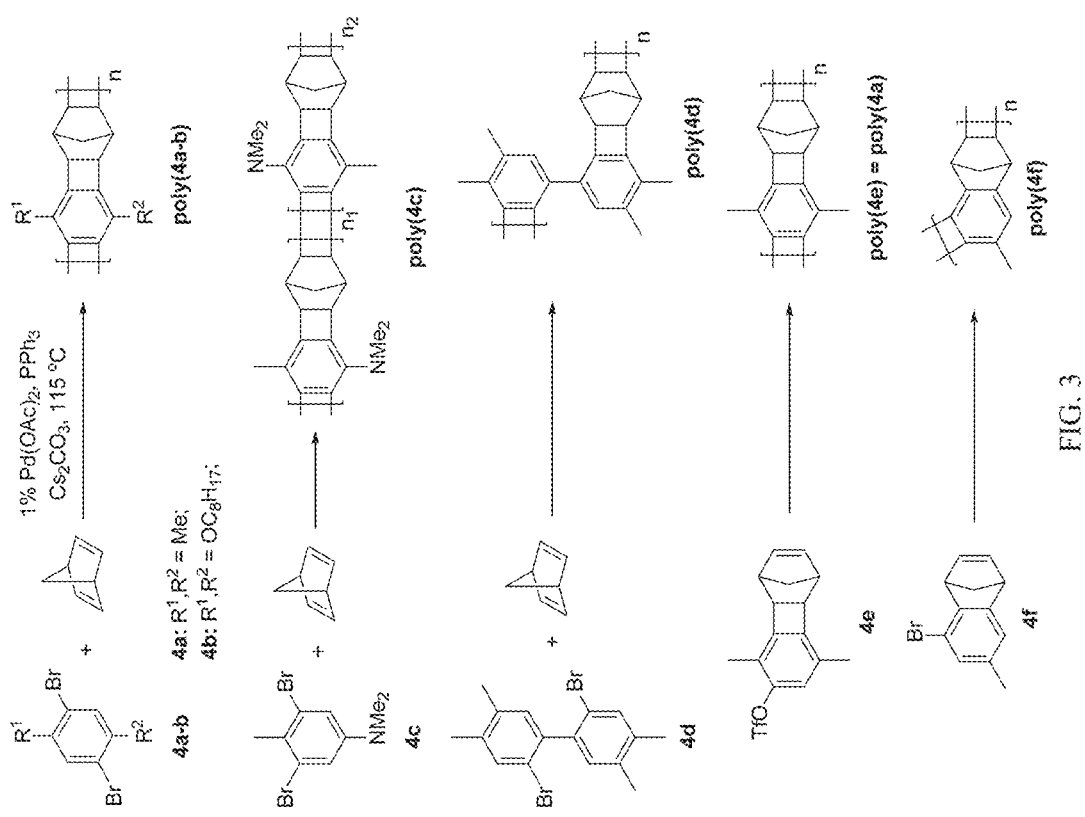
FIG. 3: Synthesis of various benzocyclobutene ladder polymers.
Figure 4:
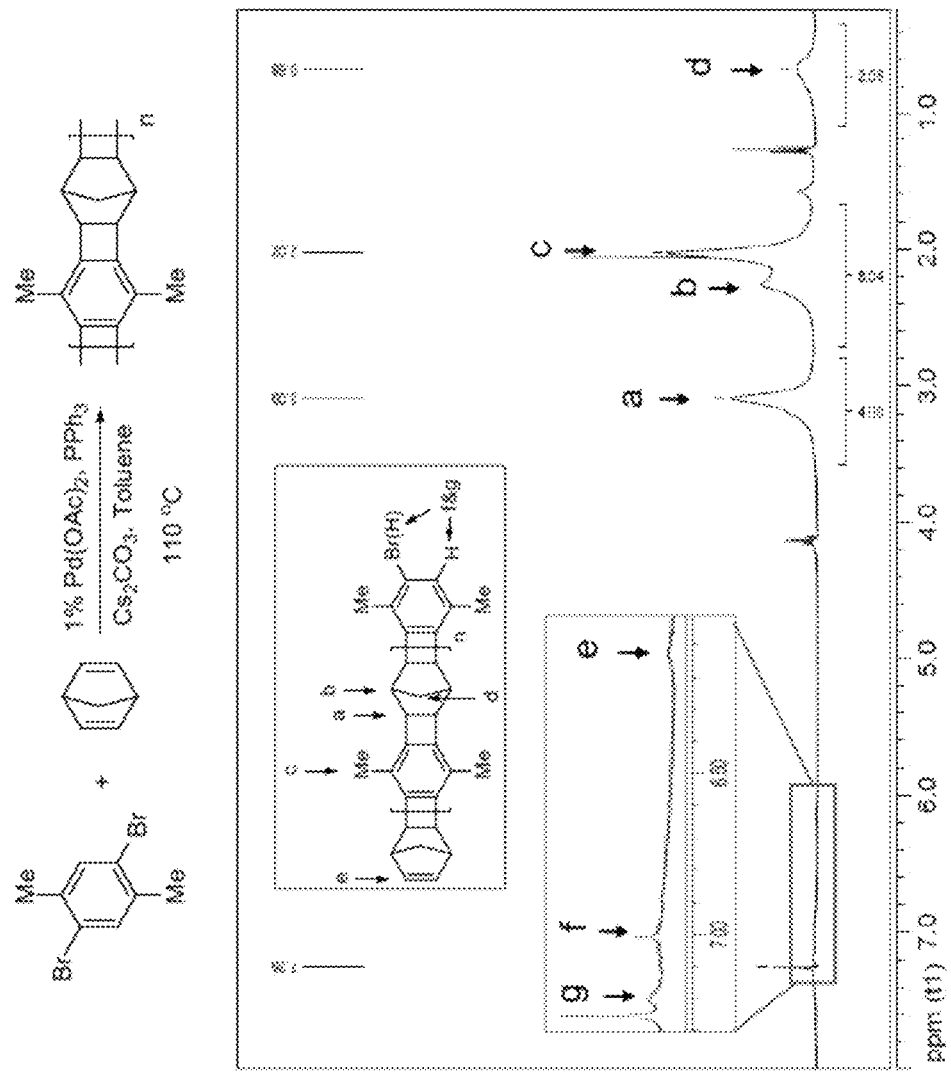
FIG. 4: Example of palladium-catalyzed ladder polymerization. $^1$H NMR spectrum of resulting ladder polymer in $CDCl_3$ with peak assignments showing evidence of the desired backbone structure and end groups.
Figure 6:
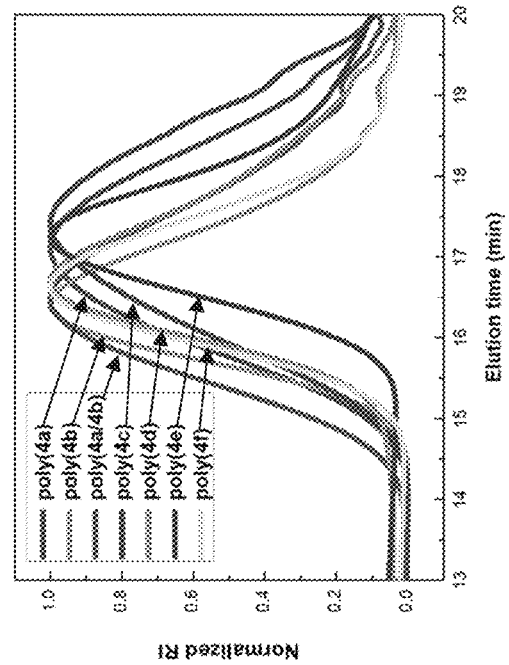
FIG. 6: Example of palladium-catalyzed ladder polymerization. Gel permeation chromatography (GPC) traces of resulting polymers, showing mono-modal molecular weight distribution over retention time (minutes). $M_n$=molecular weight; PDI=polydispersity index; and DP=degree of polymerization

Polymerization of NBD and different aryl halides 4a-c was performed (Table 2 and FIGS. 3 and 6). Polymers were obtained in quantitative conversion for electron-rich aryl halides, while electron-deficient aryl halides gave slower reactions. All ladder polymers can be dissolved in THF, and their absolute molecular weight (MW) was measured by Gel permeation chromatography (GPC) coupled with multi-angle laser light scattering (MALLS) detector. The efficient polymerization resulted in substantially mono-modal MW distribution and high MWs in the range of about 10-40 kDa. Ladder polymers with smaller substituents (e.g., methyl or methoxy) have lower solubility, especially for high MW ladder polymers, which precipitated out of the polymerization reaction at high concentrations and were soluble in chloroform. Therefore, polymerizations were performed at about 0.1 M for about 16 hours. $^1$H and $^{13}$C NMR spectroscopy indicated selective BCB ladder backbone and expected end group signals of olefin from NB and of arene protons from aryl bromide and debrominated arene (FIG. 4).

To obviate precise loading of 1:1 ratio of AA and BB types of monomers for step-growth polymerization, synthesis was performed of AB-type monomers 4e and 4f that include NB and aryl trifluoromethanesulfonate (TfO) or bromide groups (FIG. 3). 4e and 4f polymerized efficiently to produce ladder polymers. Their polymerizations were stopped after about 12 hours to ensure the polymer's solubility in THF for GPC characterization. Additionally, synthesis was performed of a biphenyl halide monomer 4d, which represents another type of accessible monomers that provide the resulting ladder polymer a certain degree of bending freedom in one direction from a biphenyl bond. Indeed, the clean chemistry allowed synthesis of telechelic ladder polymers with NB end groups. NB is a reactive functional group that can be used for crosslinking, attaching the ladder polymers to surfaces, or synthesizing block copolymers. For example, olefin metathesis can be performed to crosslink a ladder polymer and grow two end blocks from ladder chain ends.

TABLE 2

Polymerization of Aryl Halides and Dienes to Form Rigid Ladder

| entry[a] | monomer(s) | $M_n$[b] (kDa) | PDI[c] |
|---|---|---|---|
| 1 | 4a + NBD | 29 | 1.38 |
| 2 | 4b + NBD | 13 | 1.34 |
| 3 | 4c | 36 | 1.36 |
| 4 | 4d | 13 | 1.66 |

[a]Reaction was conducted using about 1 mol % Pd(OAc)$_2$, 2 eq. PPh$_3$, 2 eq. Cs$_2$CO$_3$ in toluene or THF at about 115° C.
[b]Determined by GPC MALLS analysis in THF.
[c]PDI = polydispersity index.

Figure 8B:
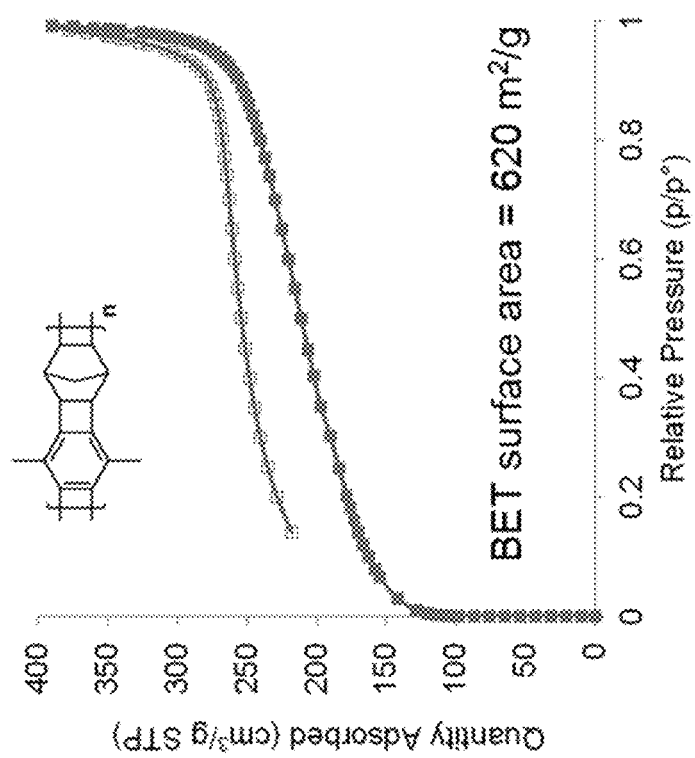
FIGS. 8A-8B: Properties of a norbornyl benzocyclobutene ladder polymer.
Figure 8A:
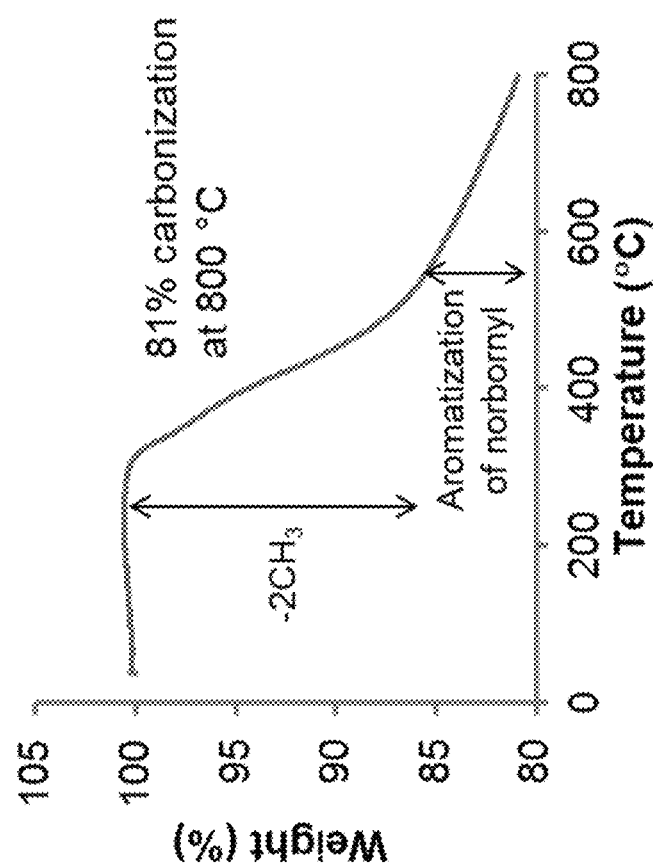

The rigid ladder backbone yields interesting properties of resulting polymers. Differential scanning calorimetry (DSC) analysis of polymer 4a showed no detectable phase transition below its partial decomposition at about 300° C. Thermal gravimetric analysis (TGA) analysis indicated that the polymer is stable up to about 300° C., and loses about 14% by weight at about 515° C., which can be attributed to the loss of two methyl substituents (FIG. 8A). Upon further heating under argon, the polymer can be carbonized with nearly 81% mass retention at about 800° C.

A semi-empirical calculation also indicated little bond rotational freedom for the BCB backbone linkage (FIG. 7). Furthermore, frustrated packing of ladder chains resulted in a large intrinsic porosity of about 620 m$^2$/g for polymer 4a, as measured by Brunauer-Emmett-Teller (BET) analysis. The combined high rigidity and large porosity render robust BCB-NB ladder polymers as promising materials for gas separation, among other applications.

By way of summary, rigid ladder polymers were efficiently synthesized via palladium-catalyzed annulation. Blocking accessibility of other reaction pathways cleanly produces ladder polymers with rigid BCB linkage at low catalyst loading. Diverse and accessible monomers can be used in the polymerization.

Example 2

Efficient Synthesis of Rigid Ladder Polymers Via Nickel-Catalyzed Annulation

The following scheme shows a model reaction for nickel-catalyzed annulation, using NiCl$_2$ as a catalyst, triphenylphosphine as a ligand, and zinc as a reducing agent in an organic solvent (tetrahydrofuran).

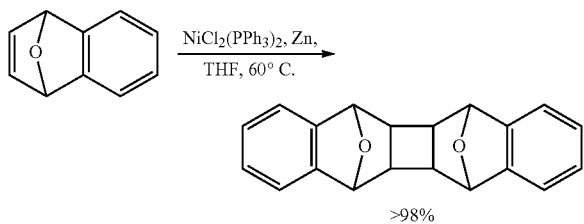

The following scheme shows a polymerization reaction to form a ladder polymer via nickel-catalyzed annulation, using NiCl$_2$ as a catalyst, triphenylphosphine as a ligand, and zinc as a reducing agent in an organic solvent (tetrahydrofuran).

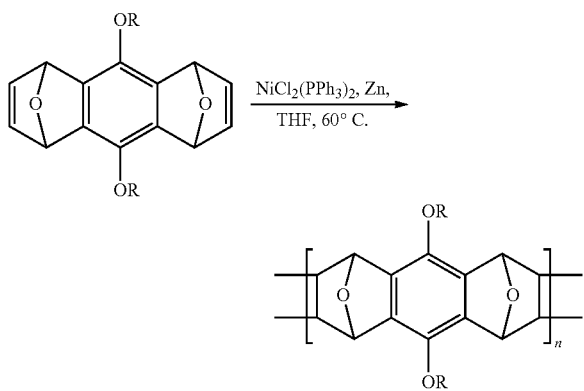

The following is a more general scheme showing a polymerization reaction to form a ladder polymer via nickel-catalyzed annulation. Nickel can be in various forms of Ni(0) or Ni(II), such as (1) Ni(0) along with a ligand, and with or without a base; and (2) Ni(II) along with a ligand, a reducing agent (such as zinc), and with or without a base.

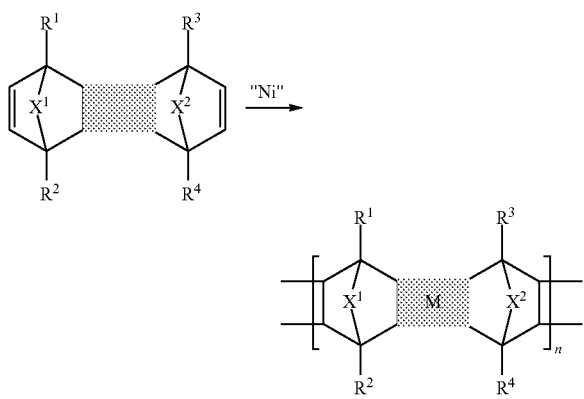

As used herein, the singular terms "a," "an," and "the" include plural referents unless the context clearly dictates otherwise. Thus, for example, reference to an object can include multiple objects unless the context clearly dictates otherwise.

As used herein, the term "set" refers to a collection of one or more objects. Thus, for example, a set of objects can include a single object or multiple objects. Objects of a set can also be referred to as members of the set. Objects of a set can be the same or different. In some instances, objects of a set can share one or more common properties.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in connection with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

As used herein, the terms "optional" and "optionally" mean that the subsequently described event or circumstance may or may not occur and that the description includes instances where the event or circumstance occurs and instances in which it does not.

As used herein, the term "group" refers to a set of atoms that form a portion of a molecule. In some instances, a group can include two or more atoms that are bonded to one another to form a portion of a molecule. A group can be monovalent or polyvalent to allow bonding to one or more additional groups of a molecule. For example, a monovalent group can be envisioned as a molecule with one of its hydrogen atoms removed to allow bonding to another group of a molecule. A group can be neutral, positively charged, or negatively charged. For example, a positively charged group can be envisioned as a neutral group with one or more protons (H$^+$) added, and a negatively charged group can be envisioned as a neutral group with one or more protons removed. Examples of groups include those set forth in the following.

As used herein, the term "alkyl group" refers to a monovalent form of a saturated hydrocarbon, such as including from 1 to 100, 1 to 50, 1 to 20, 1 to 10, or 2 to 10 carbon atoms per molecule. Examples of alkyl groups include methyl, ethyl, n-propyl, isopropyl, cyclopropyl, n-butyl, s-butyl, isobutyl, t-butyl, cyclobutyl, n-pentyl, 1-adamantyl, 2-pinenyl, and charged, hetero, cyclic, acyclic, or substituted forms thereof.

As used herein, the term "aryl group" refers to a monovalent form of an aromatic hydrocarbon, such as including from 5 to 100, 5 to 50, 5 to 20, or 5 to 14 carbon atoms per molecule. As used herein, the term "aromatic group" refers to a monovalent or a polyvalent form of an aromatic hydrocarbon, such as including from 5 to 100, 5 to 50, 5 to 20, or 5 to 14 carbon atoms per molecule. Examples of aryl groups include phenyl, biphenylyl, naphthyl, pyridinyl, pyridazinyl, pyrimidinyl, pyrazinyl, quinolyl, isoquinolyl, and charged, hetero, or substituted forms thereof.

As used herein, the term "hetero" refers to a group in which a set of its carbon atoms is replaced by a set of non-carbon atoms, such as N, Si, S, O, B, and P.

As used herein, the term "hydride group" refers to —H.

As used herein, the term "halogen group" refers to one or more of fluoro, chloro, bromo, and iodo.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

While this disclosure has been described with reference to the specific embodiments thereof, it should be understood by those skilled in the art that various changes may be made and equivalents may be substituted without departing from the true spirit and scope of this disclosure as defined by the appended claims. In addition, many modifications may be made to adapt a particular situation, material, composition of matter, method, operation or operations, to the objective, spirit and scope of this disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of this disclosure. Accordingly, unless specifically indicated herein, the order and grouping of the operations is not a limitation of this disclosure.

What is claimed is:

1. A polymer comprising at least one moiety represented by:

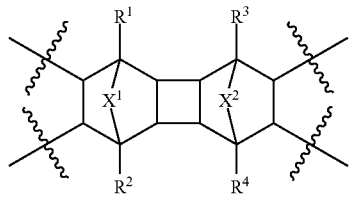

wherein $R^1$, $R^2$, $R^3$, and $R^4$ are independently selected from hydride group, alkyl groups, aryl groups, heterocyclic groups, halogen groups, groups including a —O— moiety, groups including a —O(CO)— moiety, groups including a —O(CO)O— moiety, groups including a O(CO)N< moiety, groups including a —S— moiety, groups including a —B< moiety, —NO$_2$, groups including a —N< moiety, groups including a —P< moiety, groups including a —(PO)< moiety, —CHO, groups including a —(CO)— moiety, groups including a —(CO)O— moiety, groups including a —(CO)N< moiety, or groups including a —Si≡ moiety; and wherein $X^1$ and $X^2$ are independently selected from —[O]—, —[S]—, —[B(O)$R^a$]—, —[NR$^a$]—, —[P(O)$R^a$]—, —[(PO)(O)$R^a$]—, —[CO]—, —[C(O)$R^a$(O)$R^b$]—, or —[Si(O)$R^a$(O)$R^b$]—, and $R^a$ and $R^b$ are independently selected from hydride group, alkyl groups, aryl groups, or heterocyclic groups.

2. The polymer of claim 1, comprising n instances of the moiety, and n is an integer that is greater than 1.

3. The polymer of claim 2, wherein n is 5 or greater.

4. The polymer of claim 1, comprising a first subunit including at least one instance of the moiety, and a second subunit lacking the moiety, and the first subunit is linked to the second subunit.

5. The polymer of claim 4, wherein the second subunit includes one of a polyester chain, a polyamide chain, a polyurethane chain, a polyvinyl chain, a polyether chain, or a polysiloxane chain.

6. A polymer represented by one of the following formulas:

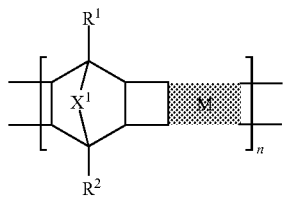

(I)

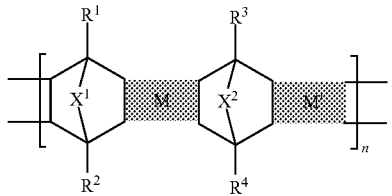

(II)

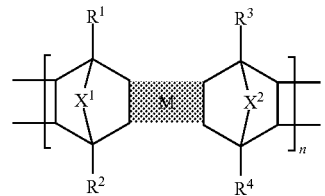

(III)

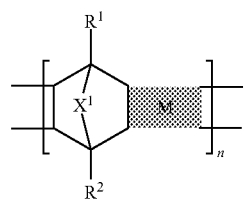

(IV)

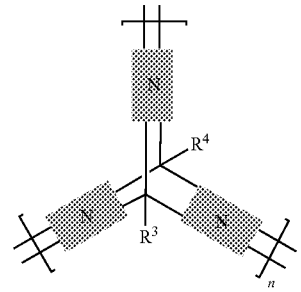

(V)

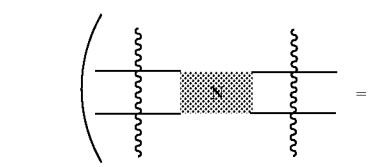

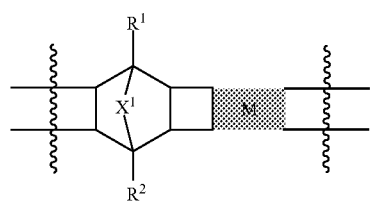

or

-continued

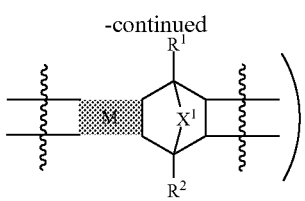

wherein $R^1$, $R^2$, $R^3$, and $R^4$ are independently selected from hydride group, alkyl groups, aryl groups, heterocyclic groups, halogen groups, groups including a —O— moiety, groups including a —O(CO)— moiety, groups including a —O(CO)O— moiety, groups including a —O(CO)N< moiety, groups including a —S— moiety, groups including a —B< moiety, —$NO_2$, groups including a —N< moiety, groups including a —P< moiety, groups including a —(PO)< moiety, —CHO, groups including a —(CO)— moiety, groups including a —(CO)O— moiety, groups including a —(CO)N< moiety, or groups including a moiety;

wherein $X^1$ and $X^2$ are independently selected from —[O]—, —[S]—, —[B(O)$R^a$]—, —[$NR^a$]—, —[P(O)$R^a$]—, —[(PO)(O)$R^a$]—, —[CO]—, —[$CR^aR^b$]—, —[C(O)$R^a$(O)$R^b$]—, or —[Si(O)$R^a$(O)$R^b$]—, and $R^a$ and $R^b$ are independently selected from hydride group, alkyl groups, aryl groups, or heterocyclic groups;

wherein M and M' are independently selected from aromatic groups or heterocyclic groups;

wherein n is an integer that is greater than 1; and wherein the polymer has a surface area of 300 $m^2$/g or more.

7. The polymer of claim 6, having a molecular weight of 4 kDa or more.

8. The polymer of claim 6, having a polydispersity index that is 4 or less.

9. The polymer of claim 6, wherein a mole ratio of hydrogen to carbon in the polymer is 1.5 or less.

10. The polymer of claim 6, having a surface area of 400 $m^2$/g or more.

11. A compound represented by the following formula:

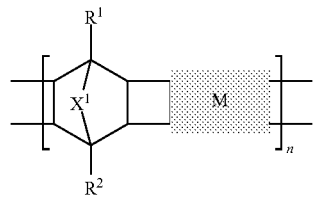

wherein $R^1$ and $R^2$ are independently selected from hydride group, alkyl groups, aryl groups, heterocyclic groups, halogen groups, groups including a —O— moiety, groups including a —O(CO)— moiety, groups including a —O(CO)O— moiety, groups including a O(CO)N< moiety, groups including a —S— moiety, groups including a —B< moiety, —$NO_2$, groups including a —N< moiety, groups including a —P< moiety, groups including a —(PO)< moiety, —CHO, groups including a —(CO)— moiety, groups including a —(CO)O— moiety, groups including a —(CO)N< moiety, or groups including a moiety;

wherein $X^1$ and $X^2$ are independently selected from —[O]—, —[S]—, —[B(O)$R^a$]—, —[$NR^a$]—, —[P(O)$R^a$]—, —[(PO)(O)$R^a$]—, —[CO]—, —[$CR^aR^b$]—, —[C(O)$R^a$(O)$R^b$]—, or —[Si(O)$R^a$(O)$R^b$]—, and $R^a$ and $R^b$ are independently selected from hydride group, alkyl groups, aryl groups, or heterocyclic groups;

wherein M is selected from aromatic groups or heterocyclic groups; and wherein n is 1 or greater.

12. The compound of claim 11, wherein n is 2 or greater.

13. The compound of claim 11, having a molecular weight of 4 kDa or more.

14. The compound of claim 11, having a polydispersity index that is 4 or less.

15. The compound of claim 11, wherein a mole ratio of hydrogen to carbon in the compound is 1.5 or less.

16. The compound of claim 11, having a surface area of 300 $m^2$/g or more.

17. The compound of claim 11, wherein M is monocyclic.

18. The compound of claim 11, wherein M is bicyclic.

19. The compound of claim 11, wherein M is tricyclic or higher order polycyclic.

\* \* \* \* \*